US012485291B2

(12) United States Patent
Canady et al.

(10) Patent No.: US 12,485,291 B2
(45) Date of Patent: Dec. 2, 2025

(54) METHOD FOR TREATMENT OF CHOLANGIOCARCINOMA WITH COLD ATMOSPHERIC PLASMA AND FOLFIRINOX

(71) Applicant: Jerome Canady Research Institute for Advanced Biological and Technological Sciences, Takoma Park, MD (US)

(72) Inventors: Jerome Canady, Lakeland, FL (US); Xiaoqian Cheng, Fairfax, VA (US); Saravana Murthy, Owings Mills, MD (US); Taisen Zhuang, Rockvillle, MD (US); Olivia Jones, Takoma Park, MD (US)

(73) Assignee: Jerome Canady Research Institute for Advanced Biological and Technological Sciences, Takoma Park, MD (US)

( * ) Notice: Subject to any disclaimer, the term of this patent is extended or adjusted under 35 U.S.C. 154(b) by 1151 days.

(21) Appl. No.: 17/135,866

(22) Filed: Dec. 28, 2020

(65) Prior Publication Data

US 2021/0196970 A1 Jul. 1, 2021

Related U.S. Application Data

(60) Provisional application No. 62/953,783, filed on Dec. 26, 2019.

(51) Int. Cl.
*A61N 1/44* (2006.01)
*A61K 31/282* (2006.01)
(Continued)

(52) U.S. Cl.
CPC .............. *A61N 1/44* (2013.01); *A61K 31/282* (2013.01); *A61K 31/4745* (2013.01);
(Continued)

(58) Field of Classification Search
CPC ......... A61B 8/042; A61B 8/1206; A61B 8/00; A61B 2018/00583; A61B 2018/00744;
(Continued)

(56) References Cited

U.S. PATENT DOCUMENTS 9,999,462 B2 6/2018 Canady et al.
10,023,858 B2 7/2018 Canady et al.
(Continued)

OTHER PUBLICATIONS

DeOliveira, M.L., S.C. Cunningham., J.L. Cameron, et al., Cholangiocurcinoma: Thirty-one-ycar experience with 564 patients at a single institution. Ann Surg, 2007. 245(5): p. 755-762.
(Continued)

*Primary Examiner* — Michael J Tsai
*Assistant Examiner* — Justin L Zamory
(74) *Attorney, Agent, or Firm* — 24IP Law Group USA, PLLC; Timothy R. DeWitt

(57) ABSTRACT

A method for a method for treatment of cholangiocarcinoma (CCA) with cold atmospheric plasma and Folfirinox. The method includes treating a patient having CCA with a low dosage FOLFIRINOX regimen, for example, 6.73 nM, giving the patient the low-dosage FOLFIRINOX regimen pre-operatively, surgically removing the cancerous tumor from the patient, continuing the low-dosage FOLFIRINOX treatment regimen intra-operatively, applying cold atmospheric plasma to the surgical margins surrounding the area in the patient from which the tumor was removed, and continuing the FOLFIRINOX post-operatively.

8 Claims, 10 Drawing Sheets

(51) Int. Cl.
*A61K 31/4745* (2006.01)
*A61K 31/513* (2006.01)
*A61K 31/519* (2006.01)
*A61P 35/00* (2006.01)

(52) U.S. Cl.
CPC .......... *A61K 31/513* (2013.01); *A61K 31/519* (2013.01); *A61P 35/00* (2018.01)

(58) Field of Classification Search
CPC .............. A61K 31/282; A61K 31/4745; A61K 31/513; A61K 31/519
See application file for complete search history.

(56) References Cited

U.S. PATENT DOCUMENTS

| | | | | |
|---|---|---|---|---|
| 10,213,614 | B2 | 2/2019 | Keidar et al. | |
| 10,329,535 | B2 | 6/2019 | Trink et al. | |
| 10,405,913 | B2 | 9/2019 | Canady et al. | |
| 2001/0043914 | A1* | 11/2001 | Mathiowitz | A61K 38/20 424/85.2 |
| 2010/0055044 | A1* | 3/2010 | Cohen | A61P 35/00 424/641 |
| 2011/0118298 | A1* | 5/2011 | Fritz | A61P 35/02 435/7.1 |
| 2014/0378892 | A1 | 12/2014 | Keidar et al. | |
| 2016/0128769 | A1* | 5/2016 | Rontal | A61B 1/00087 606/34 |
| 2016/0138006 | A1* | 5/2016 | Canady | A61B 18/042 606/34 |
| 2017/0183631 | A1 | 6/2017 | Keidar et al. | |
| 2018/0271579 | A1 | 9/2018 | Keidar et al. | |
| 2020/0060748 | A1* | 2/2020 | Cheng | A61B 18/042 |

OTHER PUBLICATIONS

Horgan, A.M., E. Amir, T. Walter, et al., Adjuvant therapy in the treatment of biliary tract cancer: A systematic review and meta-analysis. J Clin Oncol, 2012. 30(16): p. 1934-1940.

Mazzaferro, V., A. Gorgen, S. Roayaie, et al., Liver resection and transplantation for intrahepatic cholangiocarcinoma. J Ilepatol, 2020. 72(2): p. 364-37.

Shen, W.F., W. Zhong, P. Xu, et al., Clinicopathological and prognostic analysis of 429 patients with intrahepatic cholangiocarcinoma. World J Gastroenterol, 2009. 15(47): p. 5976-5982.

Marin, J.J.G., E. Lozano, E. Hcrracz, et al., Chemoresistance and chemosensitization in cholangiocarcinoma. Riochim Biophys Acta Mol Basis Dis, 2018. 1864(4 Pt B): p. 1444-1453.

Kirstein, M.M. and A. Vogel, Epidemiology and risk factors of cholangiocarcinoma. Vise Med, 2016. 32(6): p. 395-400.

Hezel, A.F. and A.X. Zhu, Systemic therapy for biliary tract cancers. Oncologist, 2008. 13(4): p. 415-423.

Penz, M., G.V. Kornek, M. Raderer, et al., Phase II trial of two-weekly gemcitabine in patients with advanced biliary tract cancer. Ann Oncol, 2001, 12(2): p. 183-186.

Lambert, A., C. Gavoille, and T. Conroy, Current status on the place of folfirinox in metastatic pancreatic cancer and future directions. Therap Adv Gastroenterol, 2017, 10(8): p. 631-645.

A., A. Karaboue, 0. Ciacio, et al., A retrospective study of patient-tailored folfirinox as a first-line chemotherapy for patients with advanced biliary tract cancer. BMC Cancer, 2020. 20(1): p. 515.

Conroy, T., F. Desseigne, M. Ychou, ct al., Folfirinox versus gemcitabine for metastatic pancreatic cancer. N Engl. I Med, 2011. 364(19): p. 1817-1825.

Dodagoudar, C., D.C. Doval, A. Mahanta, et al., Folfox-4 as second-line therapy after failure of gemcitabine and platinum combination in advanced gall bladder cancer patients. Jpn J Clin Oncol, 2016. 46(1): p. 57-62.

Schinzari, G., E. Rossi, G. Mambella, et al., First-line treatment of advanced biliary ducts carcinoma: A randomized phase ii study evaluating 5-fu/lv plus oxaliplatin (folfox 4) versus 5-fu/lv (de gramont regimen). Anticancer Res, 2017. 37(9): p. 5193-5197.

Conroy, T., P. Hammel, M. Hebbar, et al., Folfirinox or gemcitabine as adjuvant therapy for pancreatic cancer. N Engl. Med, 2018. 379(25): p. 2395-2406.

Rowe, W., X. Cheng, L. Ly, et al., The Canady Helios cold plasma scalpel significantly decreases viability in malignant solid tumor cells in a dosedependent manner. Plasma, 2018. 1(1): p. 177-188.

Barekzi, N. and M. Laroussi, Effects of low temperature plasmas on cancer cells. Plasma Processes and Polymers, 2013. 10(12): p. 1039-1050.

Barekzi, N. and M. Laroussi, Dose-dependent killing or leukemia cells by low temperature plasma. Journal of Physics D: Applied Physics, 20 I 2. 45(42).

Keidar, M., R. Walk, A. Shashurin; et al., Cold plasma selectivity and the possibility of a paradigm shift in cancer therapy. Br J Cancer, 2011. 105(9): p. 1295-301.

Arndt, S., M. Landthaler, J.L. Zimmermann, et al., Effects of cold atmospheric plasma (cap) on ss-defensins, inflammatory cytokines, and apoptosis-related molecules in keratinocytes in vitro and in vivo. PLoS One, 2015. 10(3): p. e0120041.

Bauer, G., D. Sersenova, D.B. Graves, et al., Cold atmospheric plasma and plasma activated medium trigger rans-pased tumor cell apoptosis. Sci Rep, 2019. 9(1): p. 14210.

Cheng, X., W. Rowe, L. Ly, et al., Treatment of triple-negative breast cancer cells with the Canady cold plasma conversion system: Preliminary results. Plasma, 20 I 8. 1 (1): p. 218-228.

Lee, J.II., J.Y. Om, Y.H. Kim, et al., Selective killing effects of cold atmospheric pressure plasma with no induced dysfunction of epidermal growth factor receptor in oral squamous cell carcinoma. PLoS One, 2016. 11(2): p. e0150279.

Vaquero, J., F. Judee, M. Vallette, et al., Cold-atmospheric plasma induces tumor cell death in preclinical in vivo and in vitro models of human cholangiocarcinoma. Cancers, 2020. 12(5).

Sagwal, S.K., G. Pasqual-Melo, Y. Bodnar, et al., Combination of chemotherapy and physical plasma elicits melanoma cell death via upregulation of slc22al 6. Cell Death Dis, 2018. 9(12): p. 1179.

Zhu, W., S. J. Lee, N.J. Castro, et al., Synergistic effect of cold atmospheric plasma and drug loaded core-shell nanoparticles on inhibiting breast cancer cell growth. Sci Rep, 2016. 6: p. 21974.

Masur, K., M. van Behr, S. Bekeschus, et al., Synergistic inhibition of tumor cell proliferation by cold plasma and gemcitabine. Plasma Processes and Polymers, 2015.12(12): p. 1377-1382.

Cheng, X., et al., Treatment of Triple-Negative Breast Cancer Cells with the Canady Cold Plasma Conversion System: Preliminary Results. Plasma, 2018. 1(1): p. 218-228.

Ly, L., et al., A New Cold Plasma Jet: Performance Evaluation of Cold Plasma, Hybrid Plasma and Argon Plasma Coagulation. Plasma, 2018. 1(1): p. 189-200.

* cited by examiner

METHOD FOR TREATMENT OF CHOLANGIOCARCINOMA WITH COLD ATMOSPHERIC PLASMA AND FOLFIRINOX

CROSS-REFERENCE TO RELATED APPLICATIONS

The present application claims the benefit of the filing date of U.S. Provisional Patent Application Ser. No. 62/953,783 filed by the present inventors on Dec. 26, 2019.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for treating cancer with cold atmospheric plasma.

Brief Description of the Related Art

Cholangiocarcinoma (CCA) is a rare and aggressive malignancy arising in the intrahcpatic or extrahepatic biliary tract. It is often discovered in advanced late stages, and the prognosis is poor with a five-year survival rate under 20%. DeOlivcira, M. L., S. C. Cunningham, J. L. Cameron, et al., Cholangiocurcinoma: Thirty-one-year experience with 564 patients at a single institution. Ann Surg, 2007. 245(5): p. 755-762; Horgan, A. M., E. Amir, T. Walter, et al., Adjuvant therapy in the treatment of biliary tract cancer: A systematic review and meta-analysis. J Clin Oncol, 2012. 30(16): p. 1934-40. CCAs are classified by location into intrahepatic cholangiocarcinoma (ICCA), perihilar cholangiocarcinorna (PHC), or distlil cholangiocarcinoma (DCCA) subtypes. Further ICCA has up to a 70% recurrence rate after surgical resection. Mazzaferro, V., A. Gorgen, S. Roayaie, et al., Liver resection and transplantation for intrahepatic cholangiocarcinoma. J Ilepatol, 2020. 72(2): p. 364-37. Surgical resection or liver transplantation at an early stage are the best options for curative treatment of CCA. Shen, W. F., W. Zhong, P. Xu, et al., Clinicopathological and prognostic analysis of 429 patients with intrahepatic cholangiocarcinoma. World J Gastroenterol, 2009. 15(47): p. 5976-82. Chemoresistance presents a challenge in administering adjuvant chemotherapy in all classification types and as a result, CCA is known for poor clinical outcomes. Marin, J. J. G., E. Lozano, E. Hcrracz, et al., Chemoresistance and chemosensitization in cholangiocarcinoma. Riochim Biophys Acta Mol Basis Dis, 2018. 1864(4 Pt B): p. 1444-1453; Kirstein, M. M. and A. Vogel, Epidemiology and risk factors of cholangiocarcinoma. Vise Med, 2016. 32(6): p. 395-400.

For patients with recurrent CCA, gemcitabine and fluorouracil (5-FU) have been standard options as individual treatments or drug combination therapy for years. Cisplatin plus gemcitabine versus gemcitabine for biliary tract cancer. New England Journal of Medicine, 2010; Hezel, A. F. and A. X. Zhu, Systemic therapy for biliary tract cancers. Oncologist, 2008. 13(4): p. 415-23; Penz, M., G. V. Kornek, M. Raderer, et al., Phase ii trial of two-weekly gemcitabine in patients with advanced biliary tract cancer. Ann Oncol, 2001, 12(2): p. 183-6. The FOLFIRINOX protocol is a drug regimen consisting of fluorouracil (5-FU), leucovorin, irinotecan, and oxaliplatin. This novel regimen emerged as a first line therapy in pancreatic cancers, but it is not yet standard clinical practice for CCA. Lambert, A., C. Gavoille, and T. Conroy, Current status on the place of folfirinox in metastatic pancreatic cancer and future directions. Therap Adv Gastroenterol, 2017, 10(8): p. 631-645. A small retrospective study, including 32 patients with CCA, had a patient tailored approach to FOLFIRINOX regimen and a disease control rate of 76%. Ulusakarya, A., A. Karaboue, O. Ciacio, et al., A retrospective study of patient-tailored folfirinox as a first-line chemotherapy for patients with advanced biliary tract cancer. BMC Cancer, 2020. 20(1): p. 515. In a phase two-three clinical trial, FOLFIRINOX increased overall survival over gemcitabine treatment from 6.8 to 11.1 months in patients with metastatic pancreatic cancer. Conroy, T., F. Desseigne, M. Ychou, et al., Folfirinox versus gemcitabine for metastatic pancreatic cancer. N Engl. I Med, 2011. 364(19): p. 1817-1825. However the regimen was not well tolerated; the incidence of thrombocytopenia, ncutropenia, and febrile neutropenia were significantly higher in FOLFIRINOX treatment patients. To address this limitation, studies have focused on reducing dose or modifying the four components. Dosage iterations of modified FOLFOX-4, FOLFOX-5, and FOLFOX-7 have been used to treat pancreatic, colorectal, and bladder cancers. Dodagoudar, C., D. C. Doval, A. Mahanta, et al., Folfox-4 as second-line therapy after failure of gemcitabine and platinum combination in advanced gall bladder cancer patients. Jpn J Clin Oncol, 2016. 46(1): p. 57-62; Schinzari, G., E. Rossi, G. Mambella, et al., First-line treatment of advanced biliary ducts carcinoma: A randomized phase ii study evaluating 5-fu/lv plus oxaliplatin (folfox 4) versus 5-fu/ly (de gramont regimen). Anticancer Res, 2017. 37(9): p. 5193-5197; Conroy, T., P. Hammel, M. 1-lebbar, et al., Folfirinox or gemcitabine as adjuvant therapy for pancreatic cancer. N Engl. I Med, 2018. 379(25): p. 2395-2406.

Cold atmospheric plasma (CAP) has been extensively studied in various biomedical fields. It is a novel approach to targeted cancer treatment and has demonstrated its anticancer effects in vitro. See, Rowe, W., X. Cheng, L. Ly, et al., The Canady Helios cold plasma scalpel significantly decreases viability in malignant solid tumor cells in a dose-dependent manner. Plasma, 2018. 1(1): p. 177-188; Barekzi, N. and M. Laroussi, Effects of low temperature plasmas on cancer cells. Plasma Processes and Polymers, 2013. 10(12): p. 1039-1050; Barekzi, N. und M. Laroussi, Dose-dependent killing or leukemia cells by low temperature plasma. Journal of Physics D: Applied Physics, 2012. 45(42); and Keidar, M., R. Walk, A. Shashurin; et al., Cold plasma selectivity and the possibility of a paradigm shift in cancer therapy. Br J Cancer, 2011. 105(9): p. 1295-301. The detailed mechanism has not been fully elucidated; however, studies have established that CAP selectively induces apoptosis and DNA damage in tumor cells. Arndt, S., M. Landthaler, J. L. Zimmermann, et al., Effects of cold atmospheric plasma (cap) on ss-defensins, inflammatory cytokines, and apoptosis-related molecules in keratinocytes in vitro and in vivo. PLoS One, 2015. 10(3): p. e0120041; Bauer, G., D. Sersenova, D. B. Graves, et al., Cold atmospheric plasma and plasma activated medium trigger rans-based tumor cell apoptosis. Sci Rep, 2019. 9(1): p. 14210; Cheng, X., W. Rowe, L. Ly, et al., Treatment of triple-negative breast cancer cells with the Canady cold plasma conversion system: Preliminary results. Plasma, 2018. 1 (1): p. 218-228. Further research indicates low doses of CAP does not damage normal tissue. See, e.g., Lee, J. II., J. Y.

Om, Y. H. Kim, et al., Selective killing effects of cold atmospheric pressure plasma with no induced dysfunction of epidermal growth factor receptor in oral squamous cell carcinoma. PLoS One, 2016. 11(2): p. e0150279. Recently, indirect CAP treatment was effective for the treatment of CCA in vitro, selectively killing CCA cells over normal hepatocytes. Vaquero, J., F. Judee, M. Vallette, et al., Cold-atmospheric plasma induces tumor cell death in preclinical in vivo and in vitro models of human cholangiocarcinoma. Cancers, 2020. 12(5). Research on CAP in combination with other therapies has shown some potential synergism with anti-neoplastic agents in melanoma cells (Sagwal, S. K., G. Pasqual-*Melo*, Y. Bodnar, et al., Combination of chemotherapy and physical plasma elicits melanoma cell death via upregulation of slc22al 6. Cell Death Dis, 2018. 9(12): p. 1179), drug loaded nanoparticles in breast cancer cells (Zhu, W., S. J. Lee, N.J. Castro, et al., Synergistic effect of cold atmospheric plasma and drug loaded core-shell nanoparticles on inhibiting breast cancer cell growth. Sci Rep, 2016. 6: p. 21974), and gemcitabine in murine pancreatic cancer cells (Masur, K., M. van Behr, S. Bekeschus, et al., Synergistic inhibition of tumor cell proliferation by cold plasma and gemcitabine. Plasma Processes and Polymers, 2015.12(12): p. 1377-1382).

Delivery of cold atmospheric plasma at the surgical margins immediately after tumor resection has shown potential as an anti-cancer therapy. A Canady Cold Plasma Conversion System is an electrosurgical system that produces CAP for the treatment of surgical margins upon tumor resection (U.S. Pat. No. 9,999,462). One of the advantages of cold atmospheric plasma systems is that the CAP temperature remains between 26-30° C. during the duration of the treatment (Cheng, X., et al., *Treatment of Triple-Negative Breast Cancer Cells with the Canady Cold Plasma Conversion System: Preliminary Results*. Plasma, 2018. 1(1): p. 218-228) and does not cause any thermal or physical damage to normal tissue (Ly, L., et al., *A New Cold Plasma Jet: Performance Evaluation of Cold Plasma, Hybrid Plasma and Argon Plasma Coagulation*. Plasma, 2018. 1(1): p. 189-200).

SUMMARY OF THE INVENTION

Cholangiocarcinoma (CCA) is a rare biliary tract cancer with a low five-year survival rate and high recurrence rate after surgical resection. Currently treatment approaches include systemic chemotherapeutics such as FOLFIRINOX, a chemotherapy regimen is a possible treatment for severe CCA cases. A limitation of this chemotherapy regimen is its toxicity to patients and adverse events. There exists a need for therapies to alleviate the toxicity of a FOLFIRINOX regimen while enhancing or not altering its anticancer properties. Cold Atmospheric Plasma (CAP) is a technology with a promising future as a selective cancer treatment. In this study, FOLFIRINOX treatment alone at the highest dose tested (53.8 μM fluorouracil, 13.1 μM Leucovorin, 5.1 μM irinotecan, and 3.7 μM Oxaliplatin) reduced CCA cell viability to below 20% while CAP treatment alone for 7 min reduced viability to 3% ($p<0.05$). An analysis of cell viability, proliferation, and cell cycle demonstrated that CAP in combination with FOLFIRINOX is more effective than either treatment alone at a lower FOLFIRINOX dose of 6.73 μM fluorouracil, 1.71 μM leucovorin, 0.63 μM irinotecan, and 0.47 μM oxaliplatin and a shorter CAP treatment of 1, 3, or 5 minutes. CAP reduces the toxicity burden of FOLFIRINOX. FOLFIRINOX and CAP at various dose levels to quantify changes in cell viability and cell cycle progression. FOLFIRINOX administered as a first line therapy followed by CAP treatment produces an in vitro synergistic effect.

In a preferred embodiment, the present invention is a method for treatment of cholangiocarcinoma with cold atmospheric plasma and Folfirinox. The method comprises pre-operatively treating a patient having a cholaniocarcinoma with low-dosage FOLFIRINOX not exceeding 26.91 μM fluorouracil, 6.84 μM leucovorin, 2.53 μM irinotecan, and 1.87 μM oxaliplatin, surgically removing the cholaniocarcinoma, applying cold atmospheric plasma to the surgical margins surrounding the area in the patient from which the tumor was removed, and treating the patient with low dosage FOLFIRINOX post-operatively. The method further may include treating the patient with FOLFIRINOX intra-operatively. The low-dosage FOLFIRINOX has at least 6.73 μM fluorouracil, 1.71 μM leucovorin, 0.63 μM irinotecan, and 0.47 μM oxaliplatin. In another embodiment the low-dosage FOLFIRINOX has no more than 13.45 μM fluorouracil, 3.42 μM leucovorin, 1.26 μM irinotecan, and 0.94 μM oxaliplatin.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Cholangiocarcinomas are rare with a low five-year survival rate. Cold atmospheric plasma (CAP) is a promising technology as a selective cancer treatment due to its anticancer properties. In pancreatic and liver cancers, FOLFIRINOX has emerged as an effective combination cancer drug treatment. It has been reported that FOLFIRINOX increased overall patient survival over gemcitabine treatment in patients with metastatic pancreatic cancer but is limited due to toxicity. See, T. Conroy et al., *N. Engl. J. Med.,* 364, pp. 1817-1825 (2011) and T. Conroy et al., *N. Engl. J. Med.,* 379, pp. 2395-2406 (2018).

Figure 1:
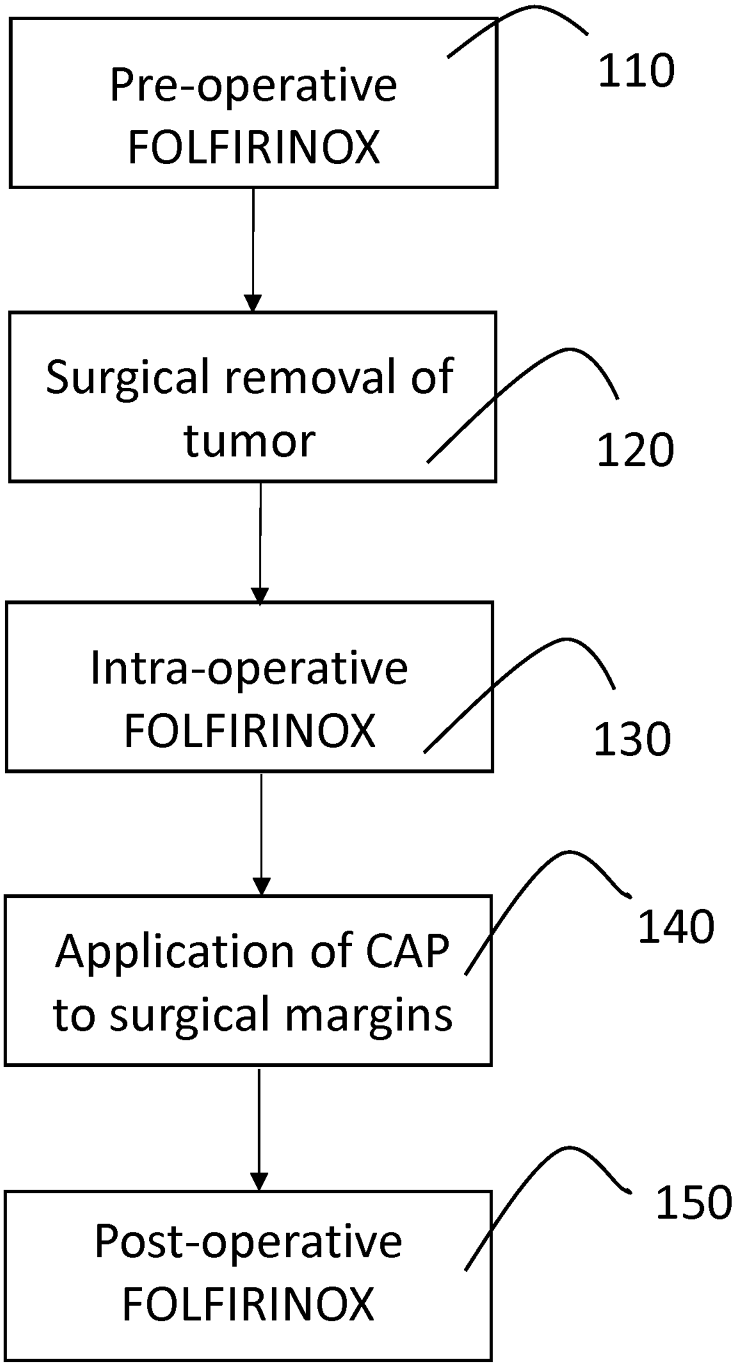
FIG. 1 is a flow chart illustrating a method for treatment of carcinoma with FOLFIRINOX and CAP in accordance with a preferred embodiment of the present invention.

A method for treating cancer with a combination of FOLFIRINOX and CAP in accordance with a preferred embodiment of the present invention is shown in FIG. 1. A patient having CCA is treated with a low dosage FOLFIRINOX regimen, for example, 6.7 μM, which is the lowest dosage found to be effective when combined with CAP. The low-dosage FOLFIRINOX regimen is started on the patient pre-operatively (110). The cancerous tumor is then surgically removed from the patient (120). The low-dosage FOLFIRINOX treatment regimen may be continued intra-operatively (130). Cold atmospheric plasma is applied to the surgical margins surrounding the area in the patient from which the tumor was removed (140). The FOLFIRINOX regimen is then continued post-operatively (150).

Figure 2:
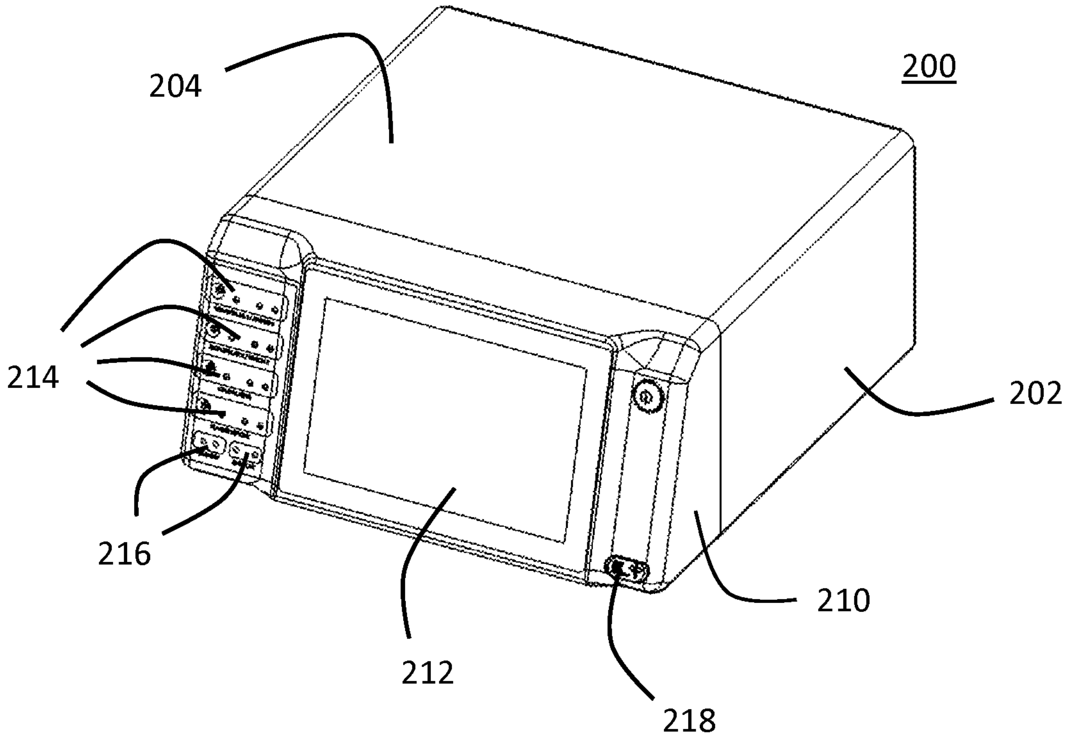
FIG. 2 is a perspective view of a preferred embodiment of a gas-enhanced electrosurgical generator that may be used in a preferred embodiment of the present invention.
Figure 3:
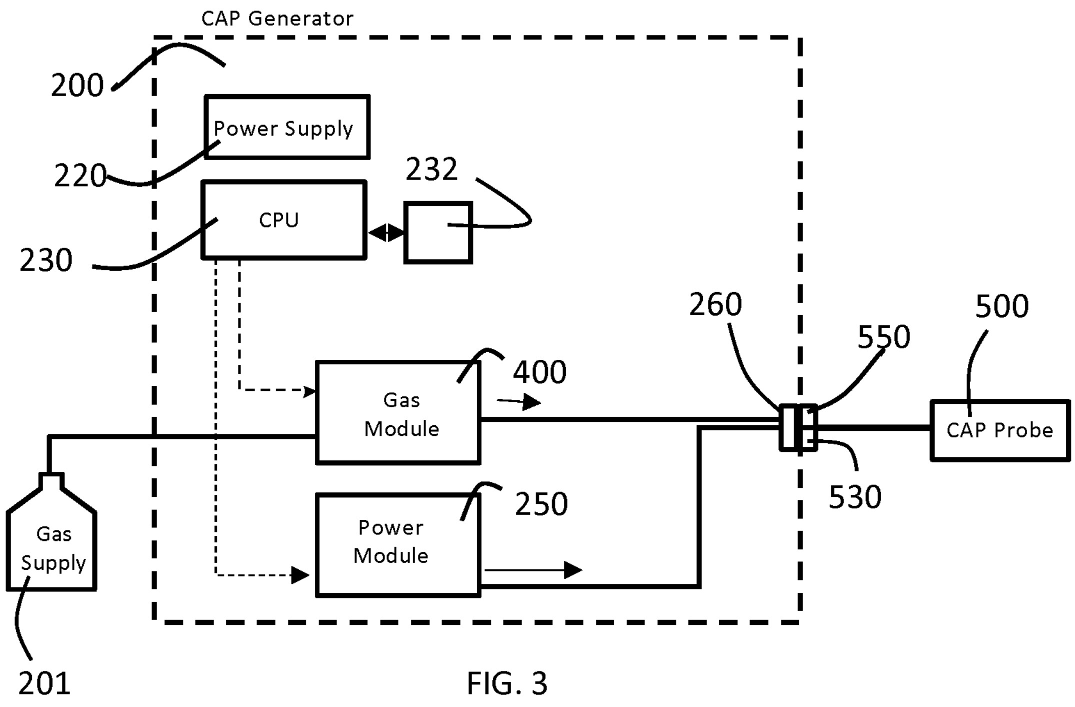
FIG. 3 is a block diagram of a cold atmospheric plasma generator in accordance with a preferred embodiment of the present invention.

A preferred embodiment of a CAP enabled generator is described with reference to the drawings. A gas-enhanced electrosurgical generator 200 in accordance with a preferred embodiment of the present invention is shown in FIGS. 2 and 3. The gas-enhanced generator has a housing 202 made of a sturdy material such as plastic or metal similar to materials used for housings of conventional electrosurgical generators. The housing 202 has a removable cover 204. The housing 202 and cover 204 have means, such as screws, tongue and groove, or other structure for removably securing the cover to the housing. The cover 204 may comprise just the top of the housing or multiple sides, such as the top, right side and left side, of the housing 202. The housing 202 may have a plurality of feet or legs (not shown) attached to the bottom of the housing. The bottom of the housing 202 may have a plurality of vents (not shown) for venting from the interior of the gas-enhanced generator.

A generator housing front panel 210 is connected to the housing 202. On the face front panel 210 there is a touchscreen display 212 and there may be one or a plurality of connectors 214 for connecting various accessories to the generator 200. For a cold atmospheric plasma generator such as is shown in FIG. 3, for example, there is a connector 260 for connecting a cold atmospheric probe 500. An integrated multi-function electrosurgical generator, such as is shown in FIG. 4B the plurality of connectors may include an argon plasma probe, a hybrid plasma probe, a cold atmospheric plasma probe, or any other electrosurgical attachment. The face of the front panel 210 is at an angle other than 90 degrees with respect to the top and bottom of the housing to provide for easier viewing and use of the touch screen display 212 by a user.

Figure 5:
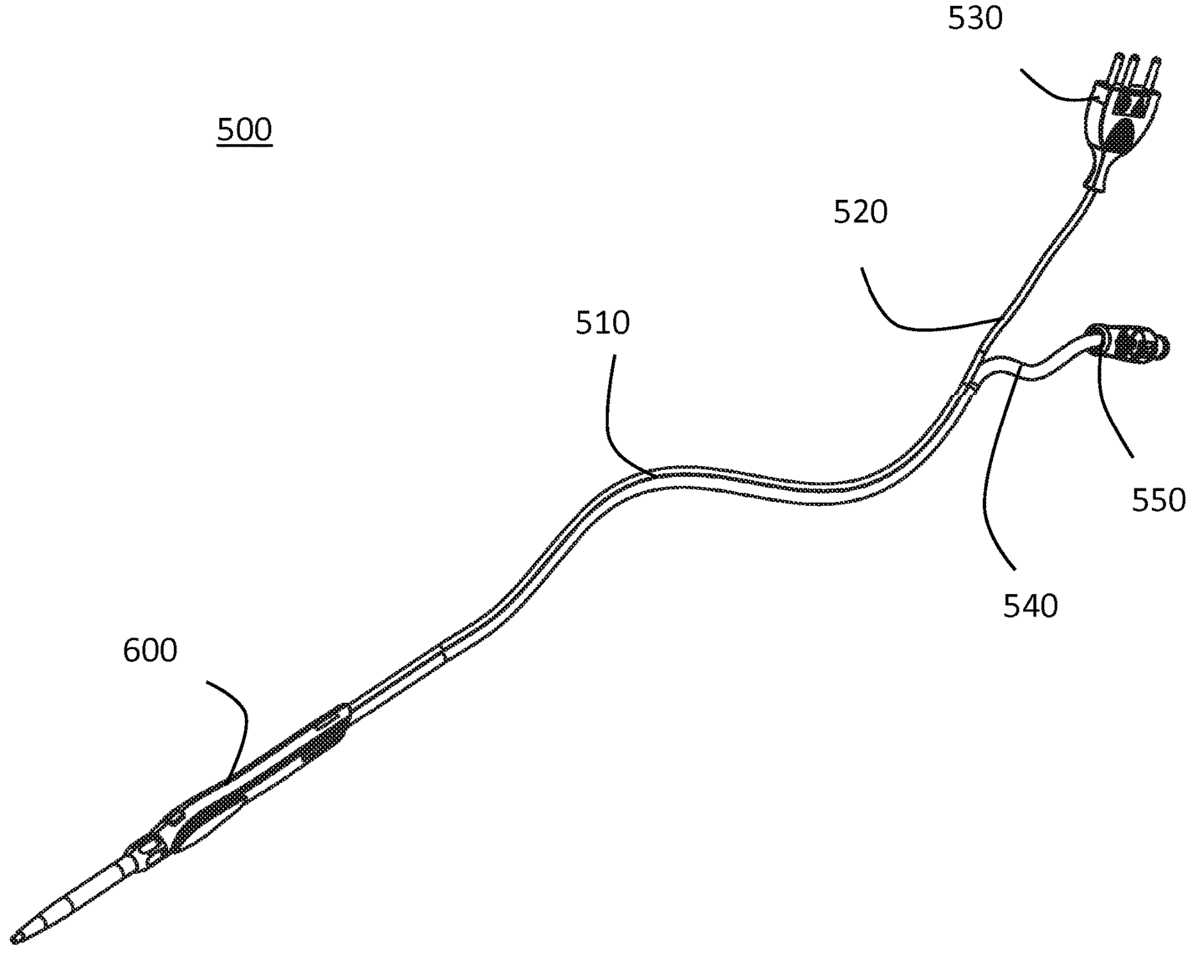
FIG. 5 is perspective view of a cold atmospheric plasma probe that may be used in a preferred embodiment of the present invention.
Figure 6A:
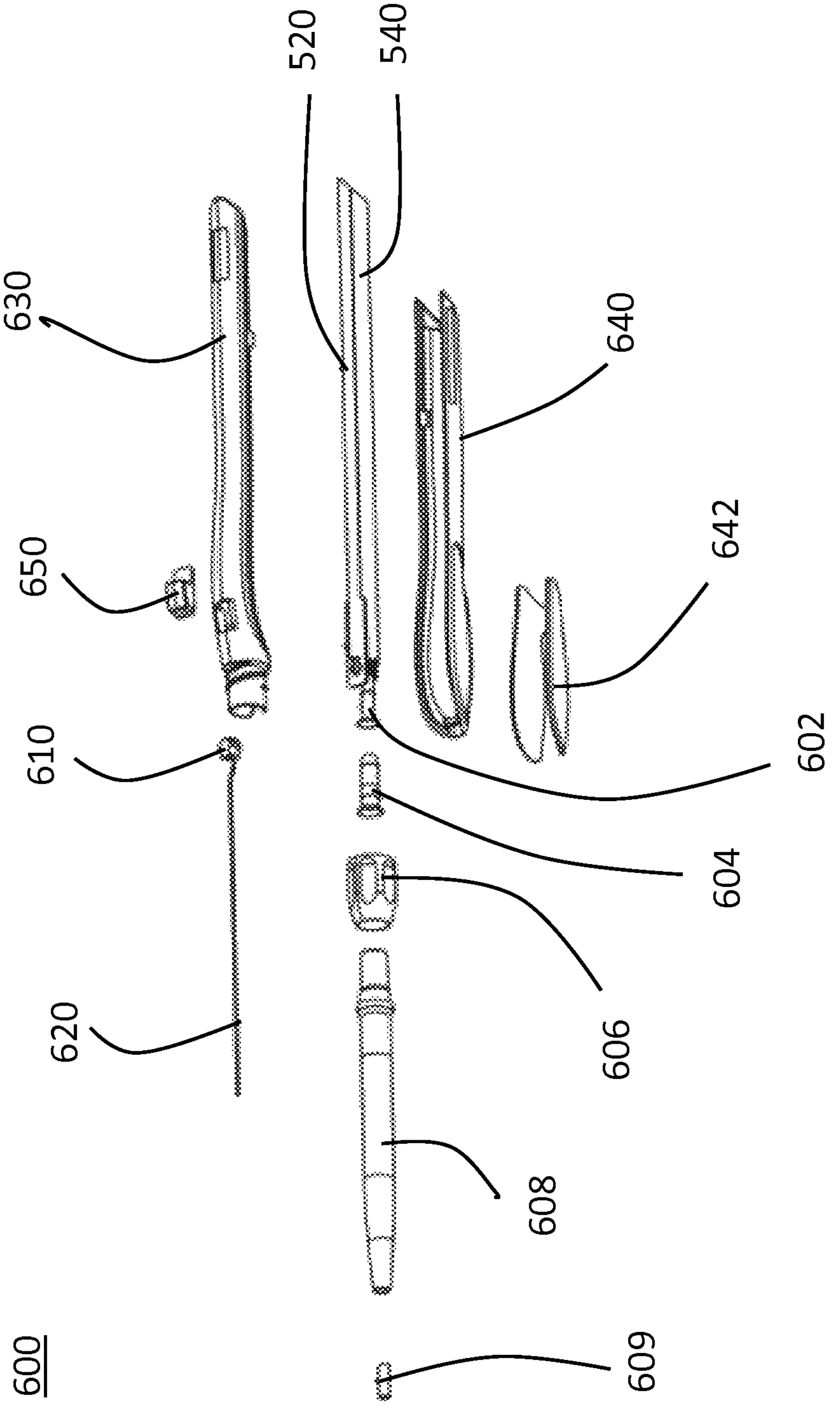
FIG. 6A is an assembly view of a handpiece of a cold atmospheric plasma probe that may be used in a preferred embodiment of the present invention.
Figure 6B:
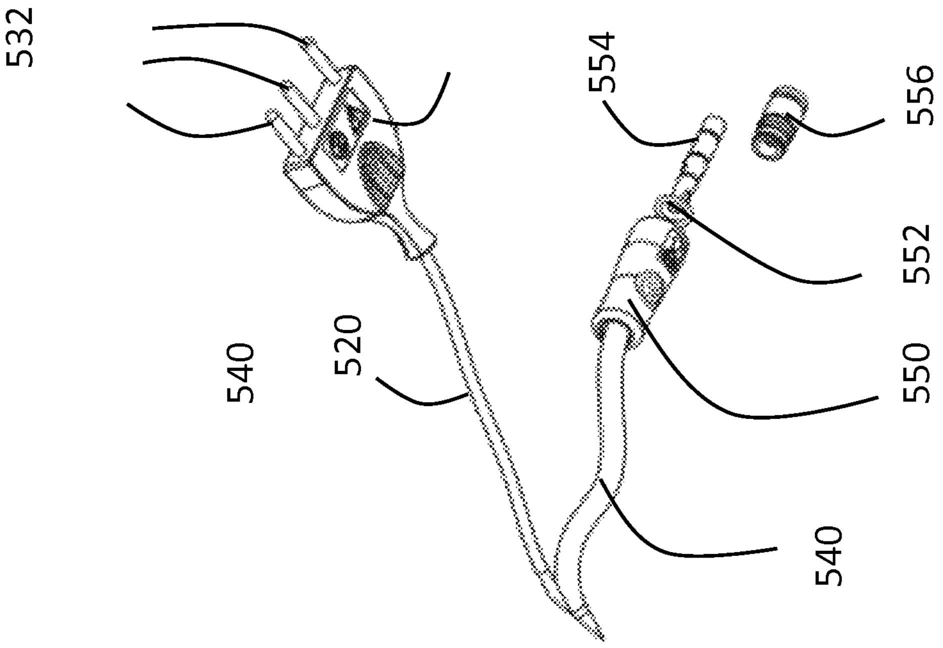
FIG. 6B is an assembly view of a cable harness of a cold atmospheric plasma probe that may be used in a preferred embodiment of the present invention.

As shown in FIG. 3, an exemplary cold atmospheric plasma (CAP) generator 200 has a power supply 220, a CPU (or processor or FPGA) 230 and a memory or storage 232. The system further has a display 212 (FIG. 2), which may be the display of a tablet computer. The CPU 230 controls the system and receives input from a user through a graphical user interface displayed on display 212. The CAP generator further has a gas control module 400 connected to a source 201 of a CAP carrier gas such as helium. The gas control module 400 may be, for example, of the design described in International Patent Application No. WO 2018/191265, which is hereby incorporated by reference. The CAP generator 200 further has a power module 250 for generating low frequency radio frequency (RF) energy, such as is described in U.S. Pat. No. 9,999,462, which is hereby incorporated by reference in its entirety. The power module 250 contains conventional electronics and/or transformers such as are known to provide RF power in electrosurgical generators. The power module 250 operates with a frequency between 10-200 kHz, which is referred to herein as a "low frequency," and output peak voltage from 3 kV to 6 kV and preferably at a frequency near (within 20%) of 40 Hz, 100 Hz or 200 Hz. The gas module 400 and power module 250 are connected to connector 260 that allows for attachment of a CAP applicator 500 (as shown in FIGS. 5, 6A and 6B) to be connected to the generator 200 via a connector having an electrical connector 530 and gas connector 550.

As shown in FIG. 4B, other arrangements for delivery of the carrier gas and the electrical energy may be used with the invention. In FIG. 4B, an integrated CAP generator **300*b* is connected to a source 310 of a carrier gas (helium in this example), which is provided to a gas control system 400, which supplies the gas at a controlled flow rate to CAP applicator 500. A high frequency (HF) power module 340*b* supplies high frequency (HF) energy to a low frequency power module (converter) 350*b*, which outputs electrical energy having a frequency in the range of 10 kHz to 200 kHz and an output voltage in the range of 3 kV to 6 Kv. This type of integrated generator will have both a CAP connector 360*b* for connecting a CAP applicator or other CAP accessory and a connector 370***b* for attaching HF electrosurgical attachments such as an argon plasma or hybrid plasma probe (not shown).

Figure 4A:
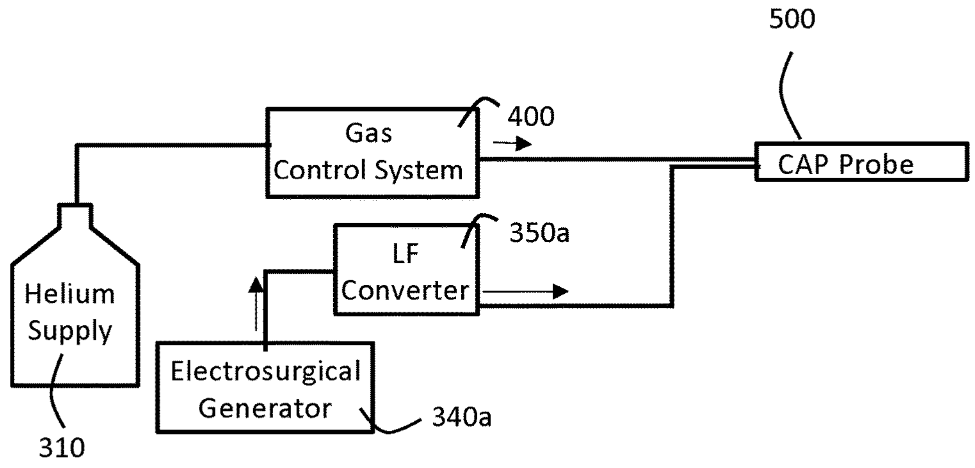
FIG. 4A is a block diagram of an embodiment of a cold atmospheric plasma system with an electrosurgical generator and a low frequency converter for producing cold plasma.
Figure 4B:
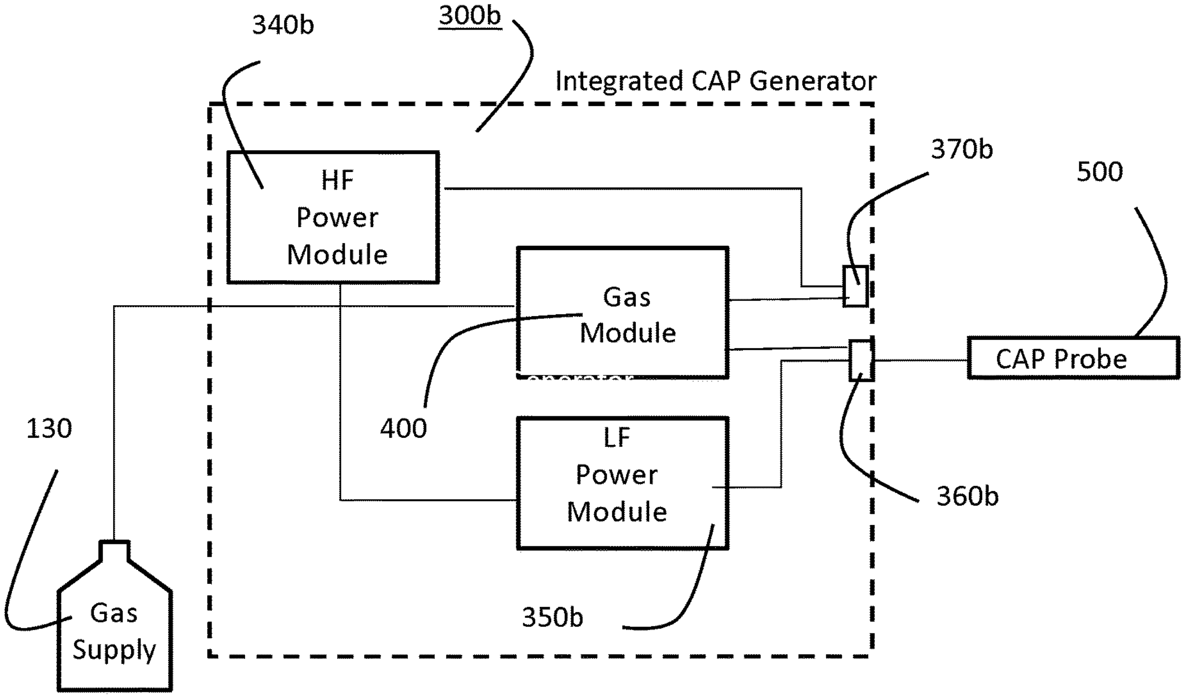
FIG. 4B is a block diagram of an embodiment of an integrated cold atmospheric plasma system that can perform multiple types of plasma surgeries.

Another embodiment, shown in FIG. 4A, has a carrier gas source 310 connected to a conventional gas control system 370, which in turn is connected to the CAP applicator 500, and a conventional electrosurgical generator 340 connected to a low frequency (LF) converter 350*a*, which is then connected to the CAP probe 500.

In the above-disclosed embodiment, a cold atmospheric plasma below 35° C. is produced. When applied to the tissue surrounding the surgical area, the cold atmospheric plasma induces metabolic suppression in only the tumor cells and enhances the response to the drugs that are injected into the patient.

The cold plasma applicator 500 may be in a form such as is disclosed in U.S. Pat. No. 10,405,913 and shown in FIGS. 5, 6A and 6B. A hand piece assembly 600 has a top side piece 630 and a bottom side piece 640. A control button 650 extends from the interior of the hand piece through an opening in the top side piece 630. Within the hand piece 600 is body connector funnel 602, PCB board 608, electrical wiring 520 and hose tubing (PVC medical grade) 540. The wiring 520 and hose tubing 540 are connected to one another to form a wire and tubing bundle 510. A grip over mold 642 extends over the bottom piece portion 640. In other embodiments, a grip may be attached to the bottom piece 640 in other manners. A probe or scalpel assembly is attached to the end of the hand piece. The probe assembly has non-bendable telescoping tubing 606, a ceramic tip 609, a column nut or collet 606 and body connector tubing 604. The hose tubing 540 extends out of the proximal end of the hand piece to a body gas connector 550, which has an O-ring 552, gas connector core 554 and gas connector tip 556 for connecting to a connector on a gas-enhanced electrosurgical generator. The printed circuit board 608 connects to electrical wiring 520 which leads to electrical connector 530 having electrical pins 532. Inside the handpiece 600 is an electrode 620 and conductive connector 610. There is a control button 650 for controlling the application of electrical energy.

Experiments

Materials and Methods

Cell Culture

The intrahepatic poorly differentiated cholangiocarcinoma cell line, KKU-055, was purchased from Sekisui XenoTech, LLC (Kansas City, KS). Cells were cultured in Dulbecco's Modified Eagle Medium (DMEM) supplemented with 10% fetal bovine serum and 1% Pen Strep (Thermo Fisher Scientific, Waltham, MA, USA). Cells were lifted with Trypsin-EDT A and seeded in 12-well plates at 100,000 cells/well or 50,000 cells/well in 1 mL complete media. Cells were then incubated 24 hours at 37° C. and 5% CO2 prior to drug or CAP treatment. All experiments were performed at the Jerome Canady Research Institution for Advanced Biological and Technological Sciences (JCRI-ABTS) in Takoma Park, MD, USA.

Cold Plasma Device

All CAP treatments were generated with a US Medical Innovations LLC 22-601 MCa high frequency electrosurgical generator, a Canady Helios™ Cold Plasma System, paired with a Canady Helios Cold Plasma™ Scalpel. All CAP tests were conducted with a constant helium flow rate of 3 L/min, at a power setting of 120p, which corresponds to 28.7 W. Treatment durations were up to 7 minutes. The distance between the tip of the plasma scalpel and media surface was constant at 1.5 cm. Immediately after CAP treatment, cells were transferred to a 37° C. and 5% CO2 humidified incubator and cultured up to 72 hours.

The four FOLFIRINOX drugs were individually diluted in DMSO then combined in a stock solution at the clinical dose ratio of oxaliplatin (Sigma Aldrich #PHR 1528) 85 mg/m2, leucovorin (Sigma Aldrich #PI JR 1541) 400 mg/1112, irinotecan (Sigma Aldrich #11406) 180 mg/m2, and 5-fiuorouracil (Sigma Aldrich #PHR 1227) 400 mg/1112. FOLFIIUNOX doses will be referred to by their corresponding concentration of 5-flourouracil [5-FU]. Further dilutions of the four drugs into the FOLFIRINOX mix were made with complete cell culture media. Cells were incubated with a single dose of drug treatment for 24 hours prior to CAP treatment.

Cell Viability Assay

Cellular viability and proliferation were assessed through a Thiazolyl Blue Tetrazolium Bromide (MTT, Abcam ab146345) assay performed 48 hours after CAP treatment. Cells were incubated with MTI solution for 3 hours at 37 and 5% CO2 humidified incubator. The absorbance of the dissolved compound was measured by BioTek Synergy I ITX (Winooski, VT, USA) microplate reader at 570 nm. Viability assays were repeated at least 3 times with a minimum of 2 intra experimental replicates. For each assay cell viability was calculated by normalizing non-treated cells.

Confocal Microscopy and Ki67 Staining

Confocal microscopy analysis was prepared in the following manner. One round platinum lined cover glass 12 mm in diameter was placed in each well of a 12-well plate then coated with fibronectin and collagen II for at least 12 hours. Cells were then seeded on cover glass inside of wells to normalize treatment to MTT assays and IncuCyte analysis. After selected drug treatment, CAP treatment, or combination treatment cultures were fixed with ice cold (−20° C.) methanol for IO minutes. Then cells were stained with Alexa Fluor 488-conjugated Ki-67 Rabbit mAh (Cell Signaling Technology, #11882) or isotype control (Cell Signaling Technology, #4340) antibodies according to Immunofluorescence General Protocol by Cell Signaling Technology (Danvers, MA, USA). Cells were incubated overnight at 4° C. protected from light. The cover slides were then carefully moved onto glass slides and covered with Anti fade Mounting Reagent with DAPI (Vector Laboratories, H-1500) drops and then a 1 mm cover slide. The slides were allowed to cure for up to 2 nights in a 4° C. refrigerator then sealed with clear nail polish.

Images were taken with Zeiss Confocal 510 LSM (Oberkochen, Germany), analyzed with Zeiss ZenLite (2012) software, and Ki-67 positivity was calculated in Microsoft Excel 2019 (Redmond, WA, USA).

Cell Cycle

Cell cycle phase contrast images were collected on the IncuCyte® Live-Cell Analysis System (Essen Bioscience, Ann Arbor, MI). A stable KKU-055 cell line was established through 5 μg/mL puromycin (Sigma Aldrich P8833) selection after transfection with the IncuCyte® Red/Green Lentivirus Reagent (IncuCyte #4779) for labelling and indication of in vitro cell cycle. Red indicated G1 phase and Green indicated S/G2/M phases while unlabeled cells indicated M-G1 transition phase or dead cells. In-vitro cell growth images were collected at 1-hour intervals up to 72 hours after each treatment condition. The percent of cell confluence and detailed cell counts per well were quantified by the IncuCyte® Cell by Cell Analysis then plotted in Microsoft Excel 2019.

Statistics

Data was plotted by Microsoft Excel 2019 as mean±standard error of the mean. Student unpaired t-tests and two-way analysis of variance (ANOVA) were used to determine significant differences between the groups. Significant CAP-drug combination effects were followed by post hoc tests with Bonferroni correction. To determine significance of independent and combined treatment groups with p-value <0.05 considered statistically significant.

Results

FOLFIRINOX Regimen Reduced Cholangiocarcinoma Cell Viability

Figure 7:
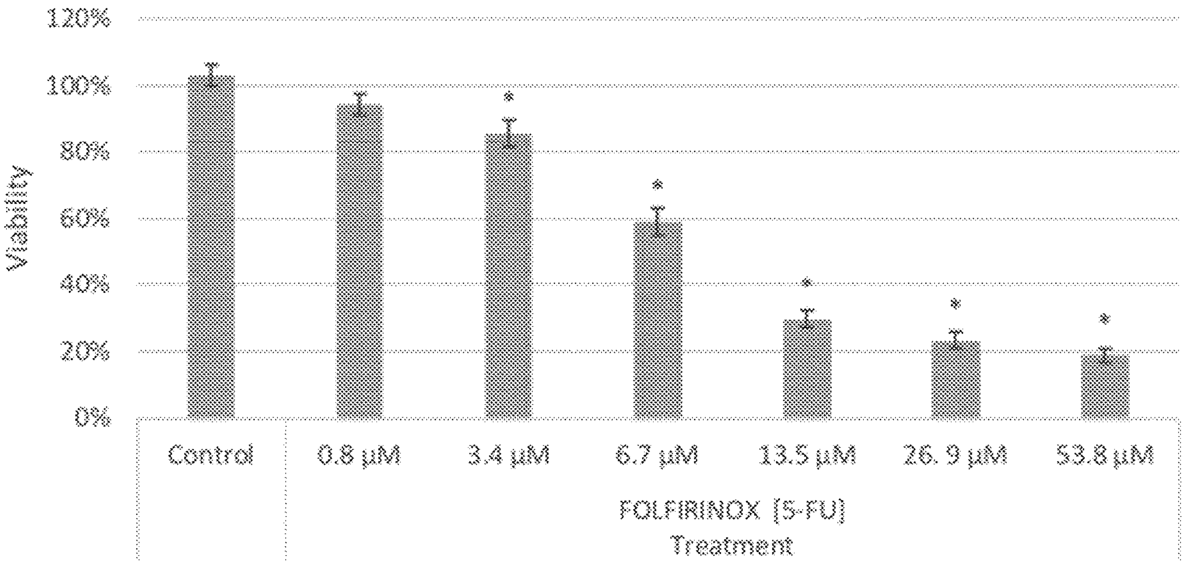
FIG. 7 is a bar graph illustrating a reduction of KKU-055 cell viability after 48-hour exposure to FOLFIRINOX, compared to DMSO treated cells controls (mean±SEM). Each drug dosage level is labeled by the corresponding concentration of 5-fluorouracil (cohort=4, 2/cohort, 11=8, t test). *P<0.05.

To determine the possible synergistic effects of FOLFIRINOX on KKU-055 cells, an optimal dosage of the four drugs in combination must be able to reduce cell viability significantly. A serial dilution of 6 doses of FOLFIRINOX was done to establish a baseline toxicity measurement for each dose (Table 1 and FIG. 7). Control cells treated with DMSO remained viable 99% (+6) suggesting that DMSO had no significant effects on cell growth, and all reduction was due to FOLFIRINOX (cohort=4, 2/cohort, n=8, t test p>0.05). Cell viability decreased significantly at doses equal to or higher than the 3.4 μM 5-FU level (cohort=4, 2/cohort, n=8, t test p<0.05). Exposure to the lowest FOLFIRINOX dose decreased viability to 94% (±3) and was not statistically significant compared to the control DMSO which reached 103% (+3). When KKU-055 cells were treated with the highest dose of FOLFIRINOX (53.8 μM Fluorouracil, 13.1 μM Leucovorin, 5.1 μM Irinotecan, and 3.7 μM Oxaliplatin), cell viability was reduced to 19% (±1.9).

Table 1 shows drug concentrations of the four FOLFIRINOX components for each dose level is the serial dilution. This corresponds to the [5-FU] notation in FIG. 7.

TABLE 1

| Drug | Dose 1 | Dose 2 | Dose 3 | Dose 4 | Dose 5 | Dose 6 |
|---|---|---|---|---|---|---|
| 5-Fluorouracil (5-FU) | 0.84 | 3.36 | 6.73 | 13.45 | 26.91 | 53.81 |
| Leucovorin | 0.21 | 0.86 | 1.71 | 3.42 | 6.84 | 13.69 |
| Irinotecan | 0.08 | 0.32 | 0.63 | 1.26 | 2.53 | 5.06 |
| Oxaliplatin | 0.06 | 0.23 | 0.47 | 0.94 | 1.87 | 3.74 |

Assessment of the Combined Treatment of CAP and FOLFIRINOX

Figure 8:
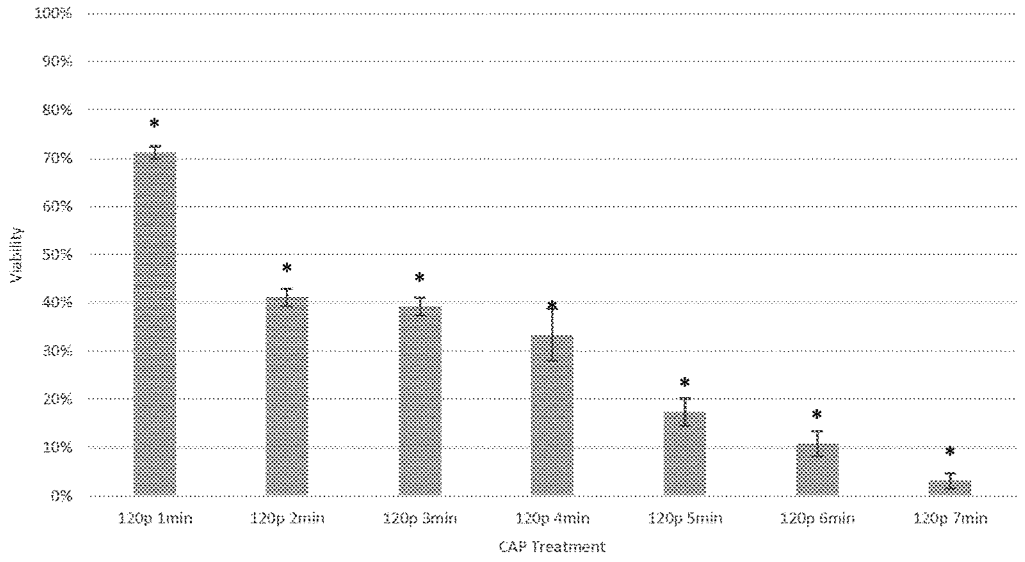
FIG. 8 is a bar graph illustrating a reduction of KKU-055 cell viability 48 hours after CAP treatment for 1-7 minutes at 120p which corresponds to 28.7 W compared to untreated controls (cohort=4, 2/cohort, n=8/test), *P<0.05.

A dose dependence experiment was performed on KKU-055 cells to establish CAP efficacy. MTT assays were conducted 48 hours post CAP treatment. Cell viability was significantly reduced by CAP for all durations, and the highest treatment of 7 minutes reduced viability to 3% (p<0.005). FIG. 8 is a bar graph illustrating a reduction of KKU-055 cell viability 48 hours after CAP treatment for 1-7 minutes at 120p which corresponds to 28.7 W compared to untreated controls (cohort=4, 2/cohort, n=8/test), *P<0.05.

Figure 9:
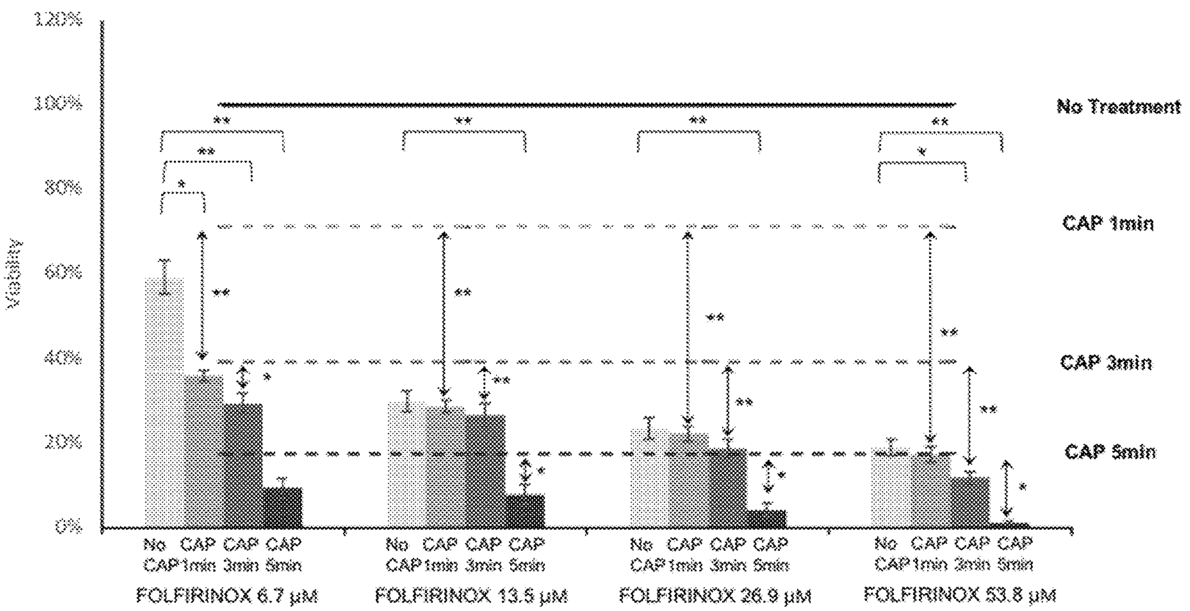
FIG. 9 is a bar graph showing the effect of adjunctive FOLFIRINOX treatment in combination with CAP on cholangiocarcinoma cell viability. Four drug dosages, labeled by their corresponding concentration of 5-fluorouracil (5-FU) from Table I, were combined with three CAP doses of either 1, 3 or 5 minutes. FOLFIRINOX treated cells were subject to 24 hours pretreatment incubation before CAP, and MTT assays were performed 48 hours utter CAP treatment. T tests were used to determine synergetic treatment combinations and arc indicated as *p<0.05 or **p<0.005.

KKU-055 cells were exposed to 24 hours of FOLFIRINOX pretreatment at 6.7-53.8 μM [5-FU](Table I) and CAP at 120p for 1, 3, or 5 minutes. Viability reduction was measured 48 hours after treatment (FIG. 9). Cells without either treatment were negative controls. Complete cell death was observed with a combination of FOLFIRINOX (53.8 μM 5-FU dose) and CAP for 5 minutes where viability was reduced to 1%.

FIG. 9 is a bar graph showing the effect of adjunctive FOLFIRINOX treatment in combination with CAP on cholangiocarcinoma cell viability. Four drug dosages, labeled by their corresponding concentration of 5-fluorouracil (5-FU) from Table I, were combined with three CAP doses of either 1, 3 or 5 minutes. FOLFIRINOX treated cells were subject to 24 hours pretreatment incubation before CAP, and MTT assays were performed 48 hours utter CAP treatment. T tests were used to determine synergetic treatment combinations and arc indicated as* p<0.05 or** p<0.005.

A two-way ANOVA test followed by post hoc Fisher exact tests (with Bonferroni correction) was conducted on this combination treatment experiment. Sources of variation were a change in either CAP dose or FOLFI RINOX dose. Then the variance between the two was tested to determine if one treatment had an effect of the other. There were three hypotheses for this test; $H_1$: The observed viability between drug dosage groups is equal; $H_2$: the observed viability between CAP dosage groups is equal; and $H_3$: there is no interaction between the two treatments. For all three hypotheses p<0.05, so we can reject each one. Student paired t-tests and two-way ANOVA test followed by post hoc Fisher exact tests (with Bonferroni correction) were then conducted to compare each combination treatment with every other experiment group (FIG. 12).

Dosage combinations were considered synergetic when combination treatment reduced viability significantly more than the corresponding CAP or FOLFIRINOX dosage alone. In cases when the FOLFIRINOX dose was 13.5 μM [5-FU] or higher the drug alone was strong enough to reduce KKU-055 viability to below 30%, and this made drug treatment significantly more effective than 1 or 3 minutes of CAP (cohort=4, 2/cohort, n=8 t test p<0.05, FIG. 9, FIG. 12). With these high doses of drug enhanced efficacy then could not be determined. The FOLFIRINOX dose (6.73 μM fluorouracil, 1.71 μM leucovorin, 0.63 μM irinotecan, and 0.47 μM oxaliplatin) in combination with 5 minutes of CAP achieved a 91% reduction in cell viability (FIG. 9) had synergistic effects at 3 minutes and 5 minutes (cohort=4, 2/cohort, n=8 t test p<0.05), and did not statistically reduce cell viability more than CAP alone so this dosage was selected for following confocal microscopy and cell cycle analysis.

Figure 12:
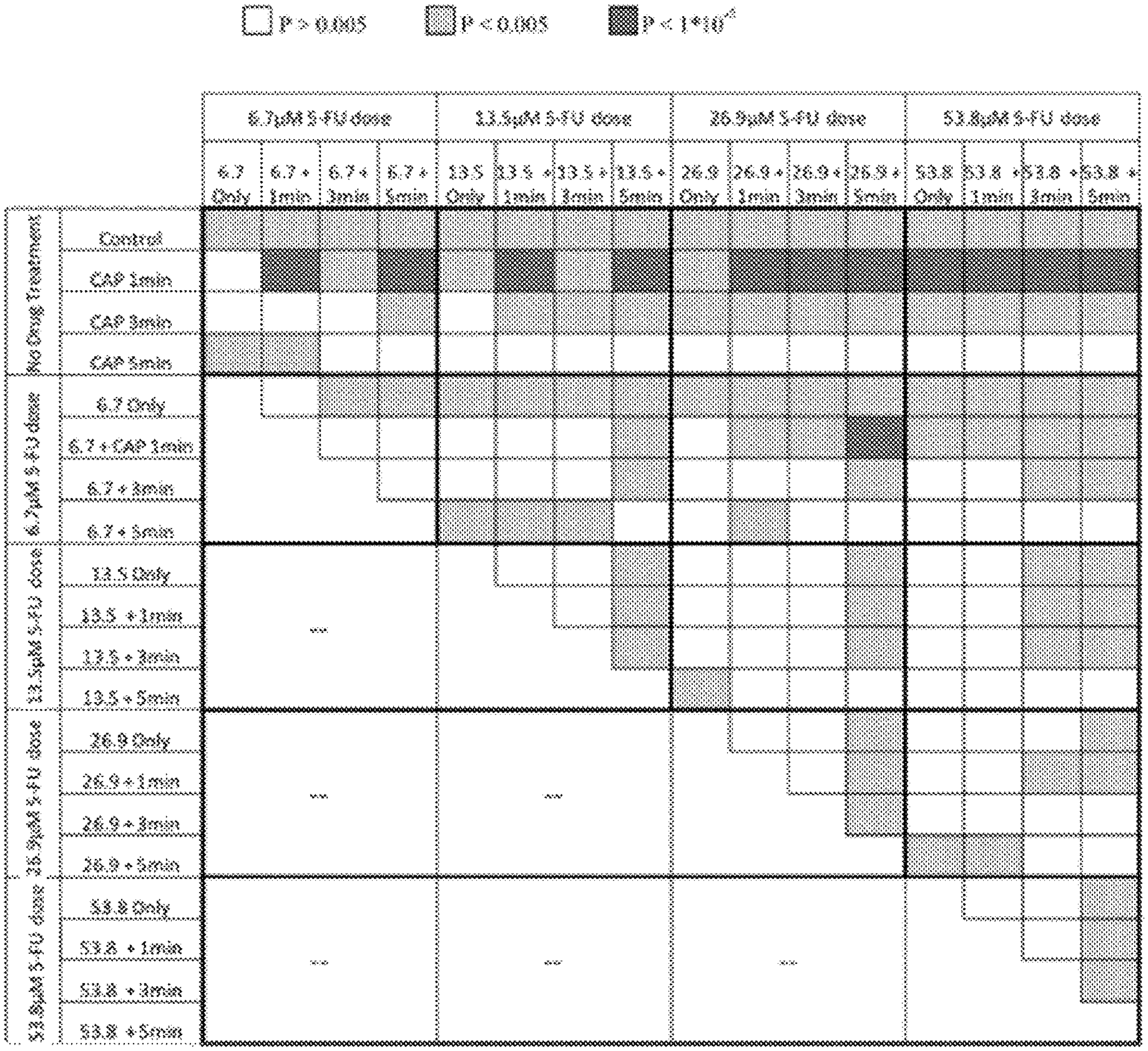
FIG. 12 is a chart showing the comparison of the reduction of viability between treatment groups.

FIG. 12 is a chart showing the comparison of the reduction of viability between treatment groups. Whether there is statistical difference p<0.005 and if that difference is extremely significant $p<1\times 10^{-5(\textit{Student's t test with Bonferroni's correction})}$.

Decrease in Cell Proliferation

Figure 10:
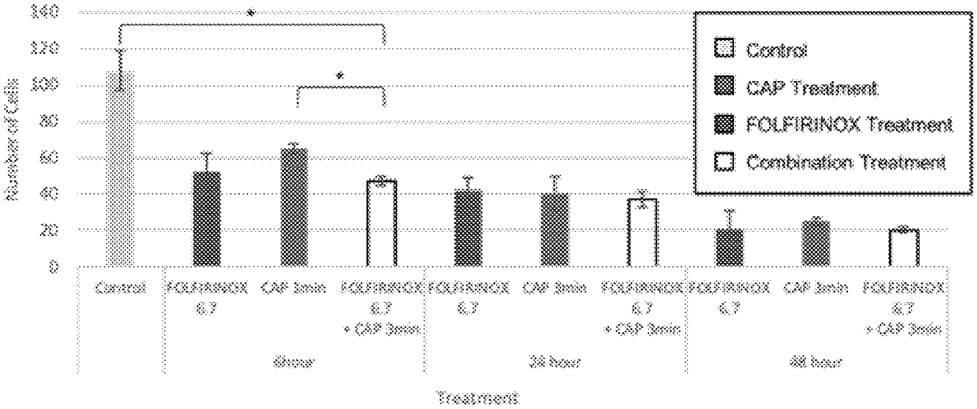
FIG. 10 is a bar graph of the total number or cells in five representative images per treatment condition is plotted (cohort=3, 2/cohort, n=6,/test), *P<0.05.

Cell proliferation was examined by Ki-67/DAPI co-staining at 6, 24, or 48 hours post CAP, FOLFIRINOX, or combination treatment. The 6.7 μM 5-FU dose of drug (Table 1) was combined with 1, 3, and 5 minutes of CAP. In five images, nuclei that were in focus were outlined and each mean fluorescence intensity (MFI) of Ki-67 channel was recorded. The mean of Ki-67 MFI was calculated for each treatment group including for No Treatment and Isotype control. A Ki-67+ cell threshold was determined as a cell with an MFI greater than the lowest mean of MFI of all groups other than Isotype control. There was a significant (cohort=3, 2/cohort, n=6, t test p<0.05) decrease in cell count with FOLFIRINOX and 3 minutes of CAP treatment combined at 6 hours compared to no treatment controls (FIG. 10). In cells treated with combination CAP 3 min and FOLFIRINOX, less cells were observed. All cells were then graded as Ki-67' or Ki-67 on this scale. In images at the 3-minute CAP timepoint and total cell counts of all timepoints, K-67 was seen to be co-localized within the outlined nucleoli in cells regardless of treatment group.

KKU-055 cells were imaged 6, 24, and 48 hours after CAP or CAP and FOLFIRINOX treatments with an untreated negative control. FIG. 10 is a bar graph of the total number or cells in five representative images per treatment condition is plotted (cohort=3, 2/cohort, n=6,/test), *P<0.05.

Induction of Cell Cycle Arrest with Combination Treatment

Experiments were designed to measure cell confluence and cell cycle distribution after combining the 6.7 μM 5-FU dose of FOLFIRINOX (Table 1) and CAP at 3 and 5 minutes. Cells were placed in the IncuCyte Live Cell imaging system immediately after CAP where confluence was monitored.

Images of 0 hours, 24 hours, and 48 hours timepoints demonstrates cell confluence within treatment wells. In the images, morphological differences were seen between experiment conditions. No treatment and drug only treated cells were confluent at 48 hours with most cells visibly fluorescent. In combination treatment wells, cells were not confluent and large clusters of cellular debris was visible after 48 hours of treatment.

Figure 11A:
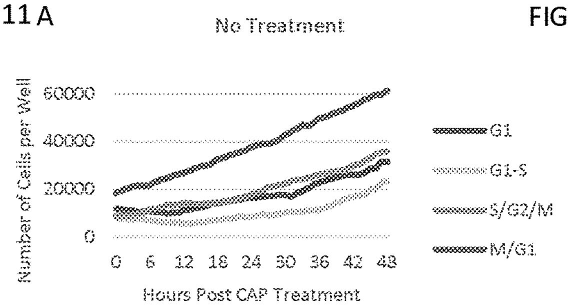
FIGS. 11A-11H are graphs of the FOLFIRINOX dosage of 6.7 μM 5-FU, 1.7 μM leucovorin, 0.6 μM irinotecan, and 0.5 μM oxaliplatin combined with CAP at 1, 3, and 5 minutes to characterize the cell cycle response. The number of cells in either G1 phase, G1-S transition, S/G2/M phase, or M-G1 transition per well in each treatment group from 0-48 hours.
Figure 11B:
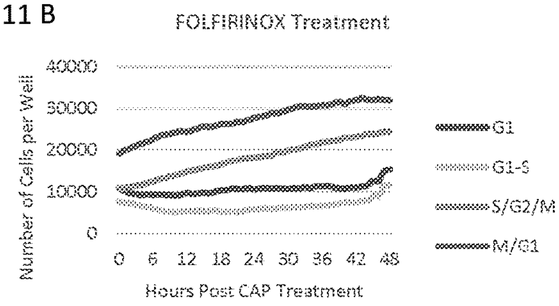
Figure 11C:
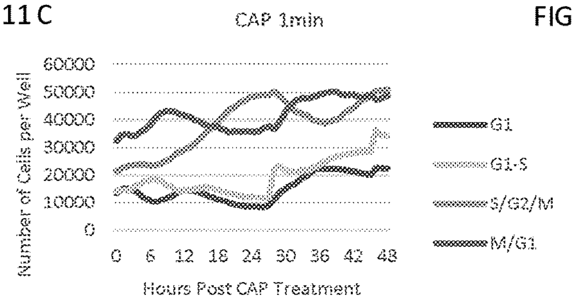
Figure 11D:
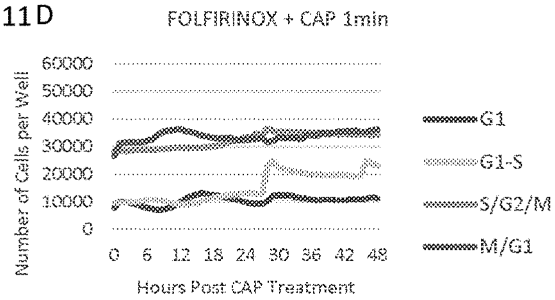
Figure 11E:
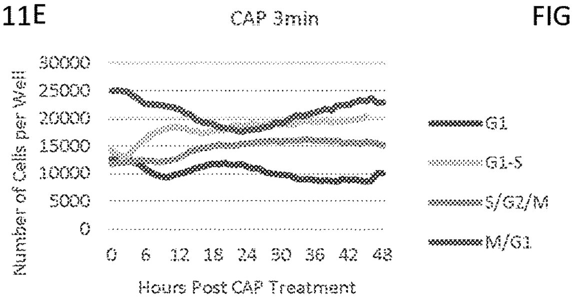
Figure 11F:
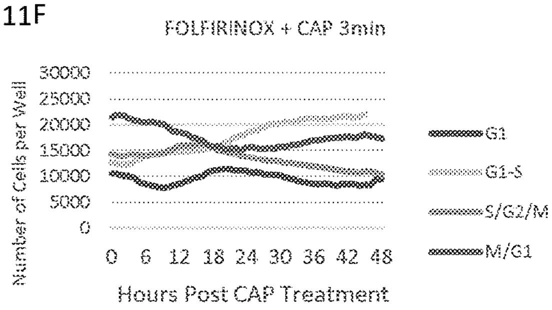
Figure 11G:
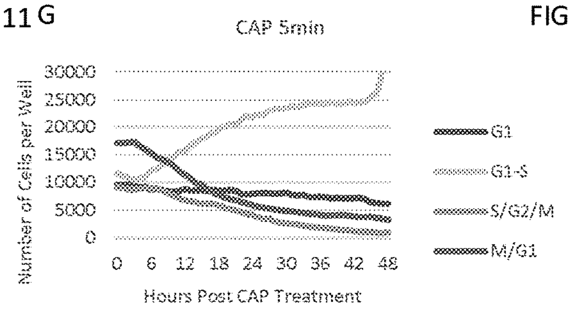
Figure 11H:
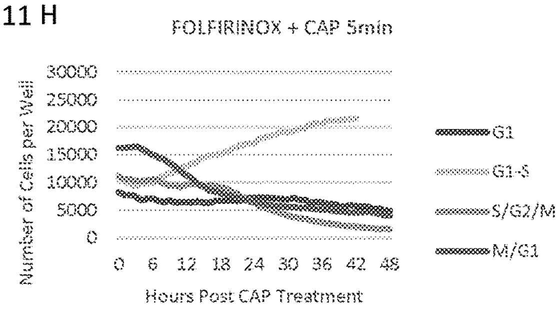

The number of cells in different phases of the cell cycle was quantified through fluorescence measurements. The quantifications during the first 48 hours after treatment are shown at the CAP 1, 3, and 5-minute doses (FIGS. 11A-11H). In the no treatment and FOLFIRINOX only treated groups, most cells are in labeled grey in the mitotic phase, and this line increases over time (FIGS. 11A-11B). Also, the number of cells in S/G2/M increases in these wells. Conversely, cells treated with FOLFIRINOX and CAP were not proliferating. At a CAP dosage of 1 minute, cells were moving through the cell cycle, as shown in the grey line (FIG. 11C). With a combination of FOLFIRINOX and CAP 1 minute this progression is reduced, and the grey line plateaued 24 hours after treatment (FIG. 11D). At CAP dosages of 3 and 5 minutes, the grey line of cells in M-G1 phase trended down after treatment. CAP and FOLFIRINOX combination treatment hindered the cell cycle, and the number of cells in the mitotic phase was reduced compared to FOLFIRINOX or a low dose (1 minute) of CAP alone. FIGS. 11G-11H were compared to the images since the presence of dead cells were counted in FIGS. 11G-11H. For example, the yellow line in FIGS. 11G-11H is not true G1-S phase signal but residual fluorescence of oxidized protein by CAP treatment as cells started to die at the 24 hours timepoint.

FIGS. 11A-11H are graphs of the FOLFIRINOX dosage of 6.7 μM 5-FU, 1.7 μM leucovorin, 0.6 μM irinotecan, and 0.5 μM oxaliplatin combined with CAP at 1, 3, and 5 minutes to characterize the cell cycle response. The number of cells in either G1 phase, G1-S transition, S/G2/M phase, or M-G1 transition per well in each treatment group from 0-48 hours.

Discussion

Cholangiocarcinoma treatment research aims to improve available chemotherapeutic options and FOLFIRINOX is promising as a novel, effective, yet toxic treatment. A clinical goal now is to establish a standard FOLFIRINOX dosage based on clinical trials. Multiple phase 1 and 2 studies are underway with encouraging results for FOLFIRINOX treatment in different doses over gemcitabine plus cisplatin, however there is no standard. The early issues in these studies are toxicity of FOLFIRINOX and early triumphs show that the regimen can be safe in patients able to tolerate it. These trials attempt to minimize toxicities by reducing or modifying drug doses because patients are excluded due to low performance status. See, Dodagoudar, C., D. C. Doval, A. Mahanta, et al., Folfox-4 as second-line therapy after failure of gemcitabine and platinum combination in advanced gall bladder cancer patients. Jpn J Clin Oncol., 2016. 46(1): p. 57-62; and Funasaka, C., Y. Kanemasa, T. Shimoyama, et al., Modiffod folfox-6 plus bevacizumab chemotherapy for metastatic colorectal cancer in patients receiving hemodialysis: A report of three cases and review of the literature. Case Rep Oncol, 2019. 12(2): p. 657-665.

CAP is a promising therapy for CCA because of its selectivity of cancer cells in bile duct, liver, and pancreatic cases in vitro. However systemic risks have not been extensively studied in clinical cases due to limited CAP use on patients. The lack of severe side effects in one cohort of 20 patients with oral cancer is encouraging. CAP has already been studied in vitro and in vivo with gemcitabine treatment, a standard option in CCA and pancreatic cancer regimens. Masur, K., M. van Behr, S. Bekeschus, et al., Synergistic inhibition of tumor cell proliferation by cold plasma and gemcitabine. Plasma Processes and Polymers, 2015, 12(12): p. 1377-1382. Liedtke, K. R., E. Freund, M. Hermes, et al., Gas plasma-conditioned ringer's lactate enhances the cytotoxic activity or cisplatin and gemcitabine in pancreatic cancer in vitro and in vivo. Cancers (Basel), 2020. 12(1); Brulle, L., M. Vandamme, D. Ries, et al., Effects of a non-thermal plasma treatment alone or in combination with gemcitabine in a mia paca2-luc orthotopic pancreatic carcinoma model, PLoS One, 2012. 7(12): p. e52653.

These reports support a combined anti-tumor effect, demonstrating that CAP has potential to increase anti-tumor effectiveness of current medicines. Recently, cold atmospheric plasma has also been studied in combination with other treatments to establish potential synergetic therapy. In this study, CAP was combined with a FOLFIRINOX regimen to treat cholangiocarcinoma cells as there exists a need to examine interactions between CAP and novel chemotherapeutics.

This study demonstrates that both CAP and FOLFIRINOX individually and in combination effectively reduce cell viability suggesting that FOLFIRINOX dosage can be reduced if paired with CAP for the treatment or CCA. Synergy was seen through MTT assays at various doses of FOLFIRINOX and CAP (FIG. 12). Confocal microscopy and IncuCyte imaging demonstrated a decrease in cell counts and changes in cell morphology after treatment which was consistent with the reduction in viability shown in FIG. 7.

This is the first study to investigate the synergistic interaction between CAP and FOLFIRINOX for the treatment of cholangiocarcinoma. Our finding of synergism between CAP and chemotherapeutics has great potential. CAP and FOLFIRINOX can be combined to reduce cholangiocarcinoma tumor cell viability and proliferation. We determined the dosage combinations in which viability reduction could be enhanced by adding 1-5 minutes of low temperature plasma to a very low dose of FOLFIRINOX (6.73 μM fluorouracil, 1.71 μM leucovorin, 0.63 μM irinotecan, and 0.47 μM oxaliplatin). A combination therapy would be advantageous for patients where an intense FOLFIRINOX regimen is too aggressive, and this warrants further clinical research. We focused on the low doses of FOLFIRINOX to reduce overall chemotherapeutic burden in vitro as a model of lower toxicity in vivo. If a lower dose of FOLFIRINOX is administered, patients with low performance status can have more treatment options. Knowledge or the interactions between CAP and chemotherapeutics is of clinical value and can lead to more personalized medicine and a lower chemotherapy burden on patients in the future.

CONCLUSION

The effectiveness of Canady Helios™ Cold Atmospheric Plasma in combination with a FOLFIRINOX regimen was explored. We found that a combination treatment can be significantly more effective than either CAP or FOLFIRINOX alone in reducing cholangiocarcinoma cell viability. We are the first to demonstrate the in vitro synergistic effect of a FOLFIRINOX treatment and CAP, and our data suggests CAP could be a possible adjuvant therapy for cholangiocarcinoma. It is important that CAP alone can selectively induce tumor cell death, however our results demonstrate that CAP can potentially reduce the dose of chemotherapeutic drugs needed for cancer patients. Future studies may examine the cellular pathways involved in these synergistic characteristics and identify the ideal dose of treatment that has the lowest feasible toxicity with the most productive outcome. This study provides insights for the clinical application of CAP for cholangiocarcinoma cancer treatment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treatment of cholangiocarcinoma comprising:

pre-operatively treating a patient having a cholaniocarcinoma with low-dosage FOLFIRINOX not exceeding 26.91 μM fluorouracil, 6.84 μM leucovorin, 2.53 μM irinotecan, and 1.87 μM oxaliplatin;

surgically removing the cholaniocarcinoma;

applying cold atmospheric plasma to the surgical margins surrounding the area in the patient from which the tumor was removed; and treating the patient with said low dosage FOLFIRINOX post-operatively.

2. A method for treatment of cholangiocarcinoma according to claim 1, wherein said low-dosage FOLFIRINOX has at least 6.73 μM fluorouracil, 1.71 μM leucovorin, 0.63 μM irinotecan, and 0.47 μM oxaliplatin.

3. A method for treatment of cholangiocarcinoma according to claim 1, wherein said low-dosage FOLFIRINOX has no more than 13.45 μM fluorouracil, 3.42 μM leucovorin, 1.26 μM irinotecan, and 0.94 μM oxaliplatin.

4. A method for treatment of cholangiocarcinoma according to claim 1, wherein said applying cold atmospheric plasma to the surgical margins comprises applying cold atmospheric plasma to the surgical margins for no more than 5 minutes.

5. A method for treatment of cholangiocarcinoma according to claim 1, wherein said applying cold atmospheric plasma to the surgical margins comprises applying cold atmospheric plasma to the surgical margins for no more than 3 minutes.

6. A method for treatment of cholangiocarcinoma according to claim 1, wherein said applying cold atmospheric plasma to the surgical margins comprises applying cold atmospheric plasma to the surgical margins for no more than 1 minute.

7. A method for treatment of cholangiocarcinoma according to claim 1, wherein said applying cold atmospheric plasma to the surgical margins comprises applying cold atmospheric plasma to the surgical margins at 120p.

8. A method for treatment of cholangiocarcinoma according to claim 1, wherein said applying cold atmospheric plasma to the surgical margins comprises applying cold atmospheric plasma to the surgical margins with a helium flow rate of 3 l/min.

* * * * *